US00PP09117P

United States Patent [19]

Christensen

[11] Patent Number: Plant 9,117

[45] Date of Patent: Apr. 25, 1995

[54] DIPLADENIA PLANT NAMED 'HELLE'

[75] Inventor: Ole V. Christensen, Aarslev, Denmark

[73] Assignee: Weidners' Gardens, Inc., Encinitas, Calif.

[21] Appl. No.: 193,546

[22] Filed: Feb. 8, 1994

[51] Int. Cl.[6] ..... A01H 5/00

[52] U.S. Cl. ..... Plt./54.1

[58] Field of Search ..... Plt. 54.1

*Primary Examiner*—James R. Feyrer

[57] ABSTRACT

A distinct cultivar of Dipladenia plant named Helle, characterized by its distinctive white flower color.

1 Drawing Sheet

The present invention relates to a new and distinctive cultivar of Dipladenia plant, botanically known as *Mandevilla sanderi* (Hemsl.), and in the trade as Dipladenia, and referred to be the cultivar name Helle, and marketed by Weidners' Gardens, Inc., of Encinitas, Calif., under the My Fair Lady trademark. The new cultivar is a color mutation from *Mandevilla sanderi.* The new cultivar was selected by me in Aarslev, Denmark, from a number of naturally-occurring mutants of *Mandevilla sanderi.*

Asexual reproduction of the new cultivar by single leaf node cuttings has shown that the unique features of this new Dipladenia are stabilized and are reproduced true to type in successive propagations. The plant was first asexually propagated by rooting single leaf node cuttings at the Research Center for horticulture in Aarslev, Denmark.

The new cultivar has not been observed under all possible environmental conditions. The phenotype may vary significantly with variations in environment such as temperature, light intensity and daylength. The following observations, measurements, values, and comparisons describe plants grown at Redland Greenhouses Holdings Pty Ltd, Redland Bay, Queensland, Australia, and Weidners' Gardens, Inc., Encinitas, Calif., USA, under commercial greenhouse conditions.

The distinctive white color of the flowers has been repeatedly observed and is determined to be the basic characteristic of Helle. This characteristic distinguishes this Dipladenia as a new and distinct cultivar.

The new cultivar is most similar to the Dipladenia cultivar Cerise and *Mandevilla sanderi* in its bushy to upright climbing habit, and continuous flowering under subtropical conditions. A comparison of the principal characteristics of those varieties with Helle appears in Chart A attached hereto. The numbers and values appearing in Chart A are based on examination of twenty randomly-selected plants from plots of 200 plants for each variety. The mean, range and standard deviation are presented for all quantitative data.

Helle is principally distinguished from Cerise and *Mandevilla sanderi* in its white flower color.

The accompanying colored photographs illustrate the overall appearance and flower color of the new cultivar, showing the colors as true as it is reasonable possible to obtain in colored reproductions of this type.

The first photograph shows a single plant of Helle compared to the cultivars Red Riding Hood and Cerise. In this photograph, the plant of Helle is older than the other two plants.

The second photograph shows an individual flower of Helle.

The following is a detailed description of my new cultivar based on plants produced under normal commercial practice in Queensland, Australia, and Encinitas, Calif. USA, under greenhouse conditions with average day temperatures ranging from 22° to 30° C. and average night temperatures ranging from 16° to 20° C.

Color references are made to the Royal Horticultural Society Colour Chart except where general terms of ordinary dictionary significance are used.

Botanical classification: *Mandevilla sanderi* (Hemsl.) cv. Helle.

Parentage: Naturally-occurring color mutant of *Mandevilla sanderi.*

Propagation:

A. *Type.*—By single leaf node cuttings.

B. *Time to initiate roots.*—42 to 56 days at temperatures of 15° to 28° C.

C. *Rooting habit.*—Fibrous, branching.

Plant description:

A. *General appearance.*—Bushy to upright climbing perennial which flowers continuously under warm (higher than 18°) night temperatures. Foliage cover is medium to dense. Stems are waxy. Flowers are abundant with fused yellow-throated corolla that is funnelform and five-parted.

B. *Foliage and stem description.*—Leaf shape and size: Numerous; opposite arrangement; pinnately veined; broadly oblong-elliptic; apex acuminate; base rounded; entire margins; on average 4 cm wide by 6 cm long; petioles are long, ranging from 5 to 11 mm; leaf morphology does not change with maturity. Leaf texture: Top and bottom sides glabrous. Leaf color: Young foliage top side: 146A with red (46A) overtones. Young foliage under side: 46A. Mature foliage top side: 147A. Mature foliage under side: 146C. Vein color: 46A. Stem color: Stem tip: 144A. Stem, 4 to 5 leaves below tip: 144A. Stem, 12 to 13 leaves below tip: 165B.

Flowering description:

A. *Flowering habit.*—Inflorescence arranged as a lateral raceme.

B. *Natural flowering season.*—Under subtropical conditions, year-round flowering.

C. *Quantity of flowers.*—Numerous inflorescences per plant, usually 4 to 7 flowers per axil.

D. *Flowers.*—Shape: Funnelform corolla, five-parted calyx. Size: Average flower diameter of 69.5 mm, average length of fused corolla is 51.5 mm. Peduncle color: 45A. Corolla color: Flower bud: During development, color changes from dark red to light pink: young bud color is 46A, progressively becoming lighter with age to 46C to 47C to 47D to 48B with mature bud color, 48D. Corolla when opening: 49D. Fully open corolla: Top side: 155B. Bottom side: 49D with swirls of 48D. Corolla fading to: 155B. Inside throat: 14B. Inside throat fading to: 9A. Outside throat: 49B.

E. *Reproductive organs.*—Stamens: Enclosed within throat, anthers connivent. Seed: Normally absent, flowers are nearly sterile.

Disease resistance: No resistance nor susceptibility to diseases have been observed.

CHART A

| Characteristic | Helle | Cerise | Mandevilla sanderi |
|---|---|---|---|
| Corolla color | white 155B | red 45A | pink 55B |

CHART A-continued

| Characteristic | Helle | Cerise | Mandevilla sanderi |
|---|---|---|---|
| Corolla throat color | 14B | 14B | 14A |
| Flower diameter | | | |
| mean | 69.5 mm | 71 mm | 66.5 mm |
| range | 58–76 | 59–78 | 57–73 |
| std. dev. | 5 | 4 | 4.5 |
| Fused corolla length | | | |
| mean | 51.5 mm | 48.5 mm | 54 mm |
| range | 49–53 | 45–51 | 51–58 |
| std. dev. | 1 | 1.5 | 2 |
| Leaf color | 147A | 147A | 141B |
| Leaf length | | | |
| mean | 58.5 mm | 63.5 mm | 70.5 mm |
| range | 52–68 | 56–74 | 64–78 |
| std. dev. | 4.5 | 4.5 | 4 |
| Petiole length | | | |
| mean | 8.5 mm | 7 mm | 7 mm |
| range | 5–11 | 6–9 | 6–9 |
| std. dev. | 1.5 | 1 | 1 |
| Stem color | | | |
| tip | 144A | 144C | 144B |
| 4–5 leaves below tip | 144A | 144A | 144C |
| 12–13 leaves below tip | 165B | 199C | 164A |

I claim:

1. A new and distinct Dipladenia plant named Helle, as illustrated and described.

* * * * *

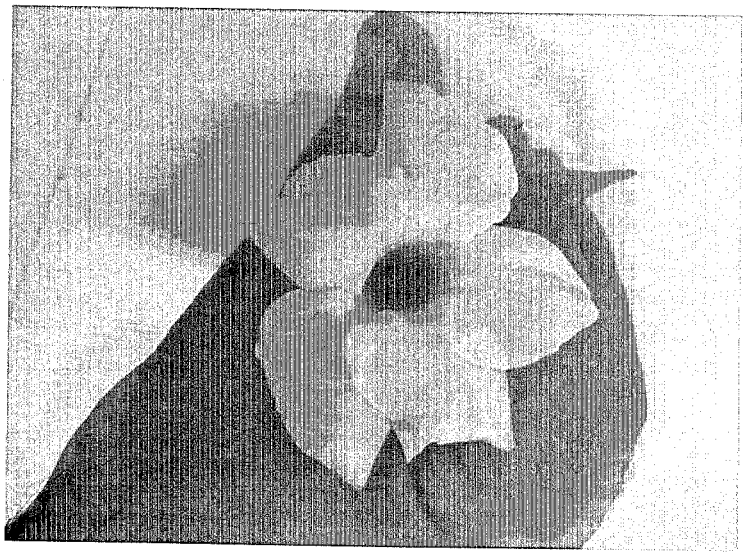

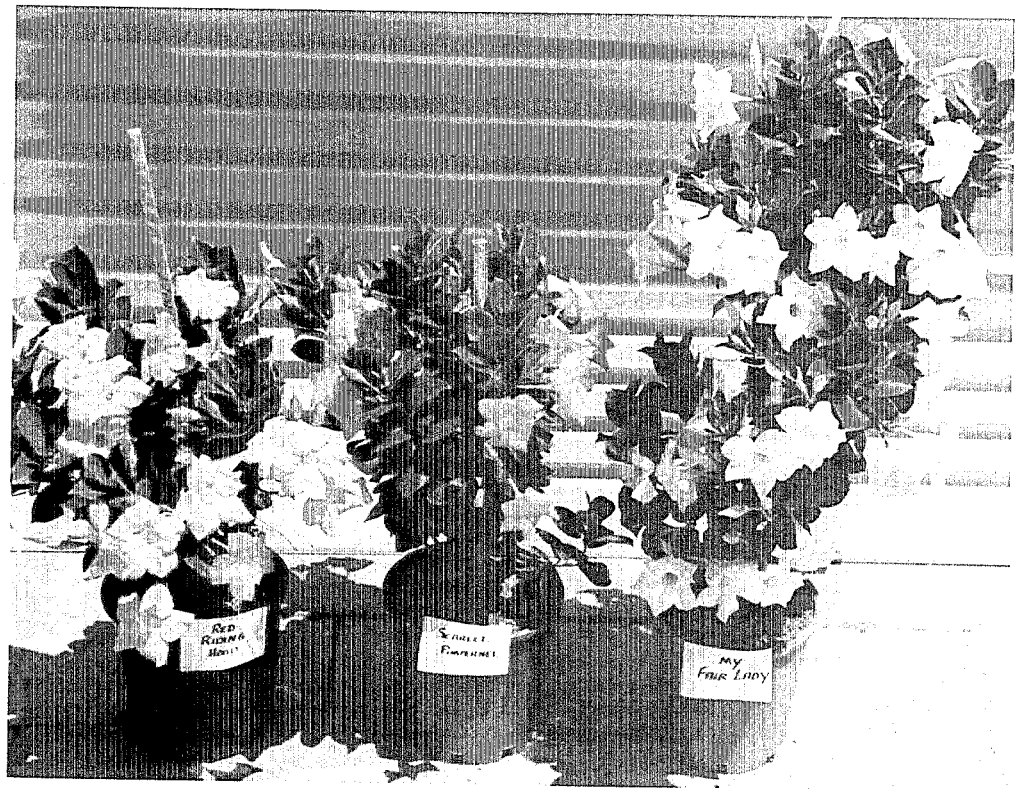
RED
RIDING
HOOD
SCARLET
PIMPERNEL
MY
FAIR LADY